(12) United States Patent  
Cohen et al.

(10) Patent No.: US 6,534,016 B1
(45) Date of Patent: Mar. 18, 2003

(54) ADDITIVE PREPARATION AND METHOD OF USE THEREOF

(76) Inventors: Richmond Cohen, 2650 Waldman Dr., Apt. 5, Williamsport, PA (US) 17701-2968; Ajit N. Dastane, 804 Amsterdam Rd., Bridgewater, NJ (US) 08807

( * ) Notice: Subject to any disclaimer, the term of this patent is extended or adjusted under 35 U.S.C. 154(b) by 15 days.

(21) Appl. No.: 09/717,417

(22) Filed: Nov. 21, 2000

Related U.S. Application Data

(63) Continuation-in-part of application No. 08/911,394, filed on Aug. 14, 1997, now Pat. No. 6,225,123.
(60) Provisional application No. 60/045,159, filed on Apr. 30, 1997.

(51) Int. Cl.[7] .................................................. B01L 3/00
(52) U.S. Cl. ............................. 422/102; 422/99; 436/8; 436/17; 436/18; 436/69; 252/408.1; 424/44; 424/466
(58) Field of Search ................................ 436/8, 17, 18, 436/69, 74, 174, 175, 177; 252/408.1; 422/99, 101, 102; 424/44, 466

(56) References Cited

U.S. PATENT DOCUMENTS

| 2,799,660 A | 7/1957 | Nicholls et al. |
| 3,105,792 A | 10/1963 | White |
| 3,136,692 A | 6/1964 | Bandelin |
| 3,852,194 A | 12/1974 | Zine |
| 3,962,107 A | 6/1976 | Levin et al. |
| 4,093,710 A | 6/1978 | Sass et al. |
| 4,153,739 A | 5/1979 | Kessler |
| 4,267,164 A | 5/1981 | Yeh et al. |
| 4,344,929 A | 8/1982 | Bonsen et al. |
| 4,451,454 A | 5/1984 | Wong |
| 4,579,828 A | 4/1986 | Ali |
| 4,650,667 A | 3/1987 | Eguchi et al. |
| 4,666,707 A | 5/1987 | Eguchi et al. |
| 4,956,300 A | 9/1990 | Wells |
| 5,002,758 A | 3/1991 | Ichii et al. |

(List continued on next page.)

FOREIGN PATENT DOCUMENTS

| EP | 0 300 221 A2 | 1/1989 |
| EP | 0 670 160 A1 | 9/1995 |
| EP | 0 775 654 A1 | 1/1997 |
| EP | 0 875 756 A2 | 11/1998 |
| JP | 361277611 A | 12/1986 |
| JP | 7-71637 | 3/1995 |
| JP | 7-71642 | 3/1995 |
| JP | 7-89157 | 4/1995 |
| WO | WO 97/02011 | 1/1997 |

*Primary Examiner*—Maureen M. Wallenhorst
(74) *Attorney, Agent, or Firm*—Nanette S. Thomas, Esq.; Scott J. Rittman, Esq.

(57) ABSTRACT

The present invention is an additive preparation which contains an additive, an organic acid, a metal carbonate compound, and a surfactant agent which is capable of rendering the surface of a collection device to have properties that cause the surface to repel the adsorption of components of a body fluid sample. The preparation effervesces when in contact with a body fluid sample, thereby efficiently dispersing the additive and surfactant in a body fluid sample.

22 Claims, 1 Drawing Sheet

U.S. PATENT DOCUMENTS

| | | | | |
|---|---|---|---|---|
| 5,096,607 | A | 3/1992 | Mowrey-McKee et al. | |
| 5,110,603 | A | 5/1992 | Rau | |
| 5,114,647 | A | 5/1992 | Levesque et al. | |
| 5,232,111 | A | 8/1993 | Burns | |
| 5,246,666 | A | 9/1993 | Vogler et al. | |
| 5,297,561 | A | 3/1994 | Hulon | |
| 5,320,812 | A | 6/1994 | Harper | |
| 5,326,535 | A | 7/1994 | Vogler et al. | |
| 5,378,431 | A | 1/1995 | Vogler et al. | |
| 5,384,062 | A | 1/1995 | Eoga et al. | |
| 5,409,662 | A | 4/1995 | Hirai | |
| 5,455,009 | A | 10/1995 | Vogler et al. | |
| 5,464,776 | A | 11/1995 | Vogler et al. | |
| 5,480,652 | A | 1/1996 | Bru-Magntez et al. | |
| 5,494,817 | A | 2/1996 | Chen | |
| 5,511,558 | A | 4/1996 | Shepard et al. | |
| 5,527,540 | A | 6/1996 | Gergely et al. | |
| 5,556,643 | A | 9/1996 | Bohanon et al. | |
| 5,567,389 | A | 10/1996 | Birbara et al. | |
| 5,593,639 | A | 1/1997 | Makino et al. | |
| 5,634,474 | A | 6/1997 | Grippi | |
| 5,646,131 | A | 7/1997 | Badwan et al. | |
| 5,738,670 | A | 4/1998 | Grippi | |
| 5,745,227 | A | 4/1998 | Dufresne et al. | |
| 5,779,983 | A * | 7/1998 | Dufresne et al. | 422/102 |
| 5,906,744 | A * | 5/1999 | Carroll et al. | 210/516 |
| 6,001,087 | A * | 12/1999 | Zurcher | 600/573 |
| 6,004,538 | A * | 12/1999 | Hughes et al. | 424/435 |
| 6,077,235 | A * | 6/2000 | Serpentino et al. | 436/18 |
| 6,136,769 | A | 10/2000 | Asano et al. | |
| 6,225,123 | B1 | 5/2001 | Cohen et al. | |

\* cited by examiner

US 6,534,016 B1

ADDITIVE PREPARATION AND METHOD OF USE THEREOF

This application is a continuation-in-part of application Ser. No. 08/911,394 filed Aug. 14, 1997, now U.S. Pat. No. 6,225,123 issued May 1, 2001, which claims priority to provisional application Ser. No. 60/045,159, filed Apr. 30, 1997.

BACKGROUND OF THE INVENTION

1. Field of the Invention

The present invention is an additive preparation for use in collection devices wherein the additive preparation effervesces when in contact with a body fluid. The additive preparation desirably comprises a formulation comprising an additive such as a clot activator, anticoagulant or urine preservation material, an organic acid, a metal carbonate compound and a surfactant agent which is capable of rendering the surface of a collection device to have properties that cause the surface to repel the adsorption of components of a body fluid sample. The effervescence effect of the formulation aids in dispersal and delivery of the additive and the surfactant agent in a body fluid sample. The formulation is desirably tableted to provide an effective, easily stored and handled preparation. In particular, the formulation of the present invention preferably comprises a clot activator or anticoagulant, an organic acid, a metal carbonate compound, and a surfactant agent wherein the formulation renders the blood collection device hemocompatible and enhances clot activation or the anticoagulant effect in a blood specimen.

2. Description of Related Art

There are many applications in the medical industry where it is desirable to have a blood collection device which has a surface which is hemocompatible. Such devices have surfaces that inhibit the adsorption of blood components such as proteins, red blood cells (RBC) and platelets. "Fouling" of the surfaces through such adsorption could render the devices less effective or even ineffective. For example, any cellular material adhering to the wall has the potential to contaminate the serum specimen if the cells lyse and release their contents. Such lysis would contaminate analytes and compromise clinical test results. It is for this reason that evacuated blood collection tubes, in particular plastic serum tubes for which adhesion of blood components to the tube wall is possible, are often coated with a surfactant which minimizes the adsorption of blood components to the wall. Plastic tubes are preferred over glass tubes in that they are resistant to breakage and therefore help to prevent the spreading of bloodborne pathogens. Currently, such plastic tubes are made of polyester (PET) and are often coated with a silicone surfactant and a particulate clot activator material such as silica. In addition to minimizing the adherence of blood components to the tube wall, the silicone surfactant enables better distribution of silica along the tube wall.

The silicone surfactant is generally sprayed onto the inner wall of the plastic tube using water as the carrier. Moreover, where both silica clot activator and silicone surfactant are to provide the coat, they may be sprayed onto the wall using polyvinylpyrrolidone (PVP) and water as the carriers. From a manufacturing stand point, the processes of coating and drying the tube wall are costly in that they are require a long time to complete and are labor-intensive.

Blood collected in evacuated tubes often must be clotted prior to clinical examination because it is desirable to form a dense clot as rapidly and completely as possible to facilitate clean separation of the clot from the serum layer by centrifugation. To achieve this end, both surfactant-coated plastic as well as glass blood collection tubes frequently employ a clot activator. Typical clot activators are diatomaceous earth and particles of inorganic silicates, or biochemicals such as ellagic acid, thrombin, trypsin and thromboplastin.

Typical clot activators used commercially are silica coated on fabric, silica particles in small plastic cups or silicate particles applied to the tube wall with a polyvinylpyrrolidone (PVP) carrier. However, in these type of arrangements, it is necessary for the user to initiate mixing of the sample so that the activator is bioavailable to the specimen thus providing the desired effect of the additive in the sample. Mixing helps to dissolve the PVP in the sample, releasing the silica to create a more uniform dispersion and enabling the silica to be held onto the tube wall. Therefore, the mixing requirement is critical to obtaining the desired effect of the additives.

Maximum effectiveness is achieved by thorough dispersion of the clot activator throughout the blood sample. Since clot activator materials are generally in powder form or as a wall coating, mixing of the clot activator with the blood sample to achieve dispersion may be a physically awkward operation. Also complete dispersion of the clot activator material in the blood sample tends to be frustrated by the tendency of the clot activator material to agglomerate upon moistening.

In addition, agglomerated clot activator particles tend to settle relatively rapidly, according to Stokes Law, which provides that the settling rate of a particle in a dispensing fluid will be governed by its relative diameter and density as well as the fluid's viscosity and density.

Therefore, there is a need for providing a means for deploying an additive in a body fluid with minimal requirements of the user to initiate mixing of the additive and the body fluid and whereby the additive is able to provide rapid and reliable performance under variable handling conditions.

Moreover, there is a need for providing a means for deploying a surfactant capable of inhibiting the adsorption of body fluid components to a surface of a body fluid collection device with minimal requirements of the user to initiate mixing of the surfactant and the body fluid and whereby the surfactant is able to be rapidly dispersed in the body fluid. One significance of not having to coat the wall prior to collection of a sample is the considerable cost savings by eliminating the long and labor-intensive processes of coating and drying the tube walls.

More particularly, there is a need for a blood collection tube with both means for rendering the surface of the tube hemocompatible at the time a blood sample is collected and means for promoting clot-acceleration of a blood sample which provides an enhanced rate of blood coagulation (shortened time for blood coagulation) without leaving any substantial amount of soluble or particulate material in the serum layer on centrifugation, thus avoiding potential interference with clinical tests, particularly in blood banking procedures. Whereas there are numerous commercial products available that employ clot activators, these products are unable to satisfactorily provide a shortened time for blood coagulation or provide a sample with minimal soluble or particulate material in the serum layer.

SUMMARY OF THE INVENTION

The present invention is an additive formulation for use in collection devices wherein the additive preparation effervesces when in contact with a body fluid. The additive preparation desirably comprises a formulation comprising an additive, an organic acid, a metal carbonate compound and surfactant capable of inhibiting the adsorption of components of a body fluid sample to a surface of a body fluid collection device.

It is desirable that the surfactant reduces the surface tension of blood to about 50 dynes/cm.

Desirably, the additive is a clot activator, anticoagulant, urine preservation material or any other body fluid preservative.

In addition, the additive formulation may further comprise a stabilizer and/or a flow improver or a binder.

Desirably, the additive formulation comprises:
 (a) from about 40 weight percent to about 90 weight percent of an additive;
 (b) from about 5 weight percent to about 30 weight percent of an organic acid or mixtures thereof;
 (c) from about 5 weight percent to about 30 weight percent of a metal carbonate compound; and
 (d) from about 2 weight percent to about 10 weight percent of a surfactant which is capable of inhibiting the adsorption of compounds of a body fluid to a surface of a body fluid collection device.

The present invention is most preferably an additive formulation for enhancing clot activation of a blood sample. The additive formulation desirably comprises a clot activator, an organic acid and a metal carbonate compound, and a surfactant which is capable of inhibiting the adsorption of blood components to a blood collection device.

Preferably, the clot activator additive formulation comprises:
 (a) about 70 weight percent to about 95 weight percent of a clot activator;
 (b) about 3 weight percent to about 15 weight percent of organic acid;
 (c) about 3 weight percent to about 15 weight percent of metal carbonate; and
 (d) about 4 weight percent to about 6 weight percent of a surfactant which is capable of inhibiting the adsorption of blood components to a blood collection device.

The additive formulation may further comprise a binding agent from about 1 weight percent to about 30 weight percent of a binder.

The clot activator may be diatomaceous earth, particles of inorganic silicates or biochemicals such as ellagic acid, thrombin, trypsin and thromboplastin or combinations thereof.

It is preferred that the surfactant is a silicone surfactant capable of reducing the surface tension of blood to about 50 dynes/cm.

A significant attribute of the additive formulation of the present invention is its use in collection devices wherein the additive preparation effervesces when in contact with a body fluid sample. The effect of the additive preparation therefore aids in the dispersal and delivery of both the additive and a surfactant to a body fluid sample. The effervescent dispersal of the surfactant renders the collection device to be compatible with the body fluid sample.

A significant attribute of the clot activator additive formulation of the present invention is its use in blood collection devices as an effective and efficient means for promoting blood coagulation in a collection device which has been made hemocompatible by the presence of a surfactant in the same formulation. Most importantly is that the additive formulation and the blood sample does not have to be mixed by the user.

An important advantage of the clot activator additive formulation of the present invention is its ease of use not requiring lengthy time to promote blood coagulation as compared to conventional techniques.

Furthermore, it is an important advantage of the additive formulation that the inclusion of a surfactant component capable of making a blood evacuated tube hemocompatible eliminates the need for a tube which has been precoated with a surfactant. Therefore, the costly and timely steps of coating and drying these tubes during manufacture thereof can be eliminated.

Notably, the formulations of the present invention rapidly disintegrate and disperse in a body fluid sample, thereby minimizing the requirement that the user assist in mixing the formulation and the body fluid sample.

DETAILED DESCRIPTION

Figure 1:
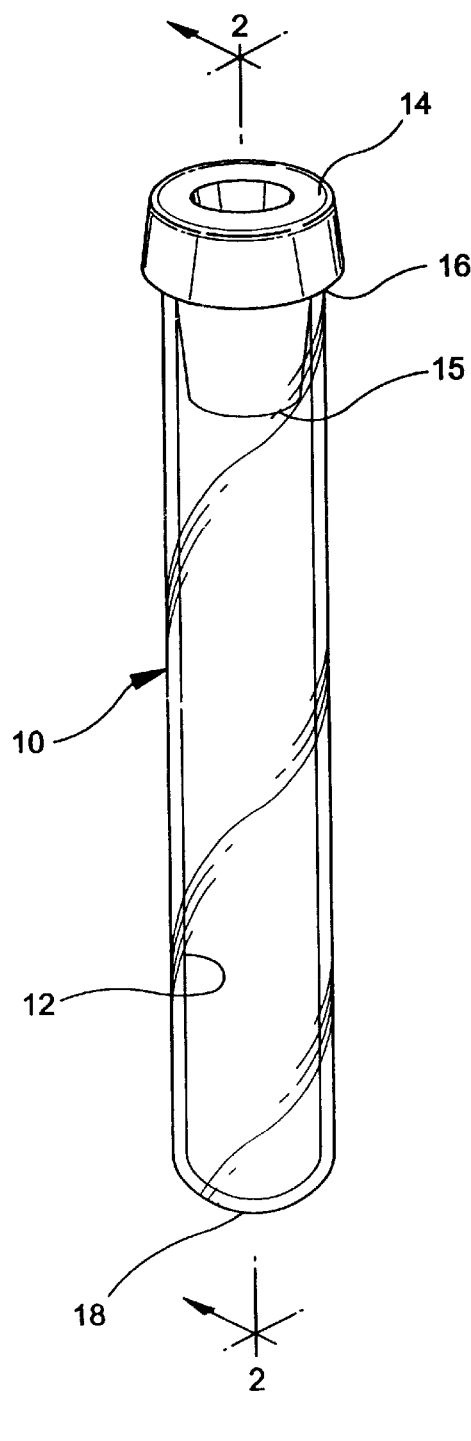
FIG. 1 is a perspective view of a typical blood collection tube with a stopper.

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The invention is for an additive preparation and method of use thereof whereby the additive preparation effervesces and disperses a substance capable of rendering a surface to have properties that cause the surface to repel body fluid components from adhering to it. In particular, this invention focuses on, but is not limited to evacuated blood collection tubes. The primary composition of the additive preparation and its value in blood collection tubes is described in U.S. application Ser. No. 08/911,394 to Cohen and Dastane, now U.S. Pat. No. 6,225,123 issued on May 1, 2001. The application discloses an effervescent additive formulation which, upon contact with blood, disperses clot activating silica particles throughout a blood collection device to effect a uniform and rapid clotting without the need to mix the tube. The present invention adds an agent to the additive preparation disclosed therein which renders the blood collection device hemocompatible when dispersed throughout the tube. The present invention reduces or eliminates the need to precoat the surface of the blood collection tube wall with a surfactant.

The additive formulation of the present invention comprises:
 (a) from about 40 weight percent to about 90 weight percent of a clot activator;
 (b) from about 5 weight percent to about 30 weight percent of an organic acid;
 (c) from about 5 weight percent to about 30 weight percent of a metal carbonate; and
 (d) from about 2 weight percent to about 10 weight percent of a surfactant which is capable of inhibiting the adsorption of blood components to a blood collection device.

In one embodiment the surfactant is capable of reducing the surface tension of blood to about 50 dynes/cm. It is preferred that the surfactant reduces the surface tension of blood from about 30 dynes/cm to about 45 dynes/cm.

Without wishing to be bound by only one theory, it is believed that compositions of the present invention, which include surfactants, lower the surface energy of the blood, thereby reducing the blood cells tendency to adsorb on the surface of body fluid collection device surfaces.

Inclusion of the surfactant agent in the additive preparation of the present invention succeeds in reducing the surface tension of blood to a level which allows for less adhesion of blood components relative to the same preparation without surfactant. It is an aspect of this invention to enable the production of a serum blood collection tube without the need to coat the wall with a surfactant and maintain the surface of the tube wall free of visible red-cell adhesion. The significance of not having to coat the tube wall is that it represents a considerable cost savings by eliminating the long and energy-intensive processes of coating and drying. In the proposed invention, the additive preparation is efficacious at providing good clotting performance and providing a wall surface that is not fouled by excessive blood proteins and cells. Furthermore, the composition is prepared and subsequently tabletted offline and rapidly dispensed into a tube online, lowering the overall cycle time for production.

Desirably, the surfactant used in the additive formulations of the present invention is a silicone which includes a hydrophobic backbone of polydimethylsiloxane and a hydrophilic tail of polyalkylether. For example, a silicone surfactant sold under the trade name Silwet-L720 by CK Witco Corporation has been found to be useful. However, surfactants useful for this invention are those capable of bringing the surface tension of the blood below about 50 dynes/cm. For example, fluorocarbon or alkylene oxide based surfactants may be employed.

In one embodiment of the present invention the surfactant is present at about 2 weight percent to about 10 weight percent of the additive preparation. It is preferred that the surfactant is present at about 3 weight percent to about 7 weight percent of the preparation. In the most preferred embodiment, the surfactant is present at about 4 weight percent to about 6 weight percent of the preparation.

A clot activator material is preferably used in the formulation to initiate rapid clotting of a blood sample that comes in contact with the formulation of the present invention.

A blood specimen often needs to be clotted to obtain serum. Serum is the specimen of choice for performing blood chemistries.

Desirably, the clot activator materials, include, but are not limited to, diatomaceous earth, inorganic silicates, ellagic acid, thrombin, trypsin and thromboplastin.

The preferred clot activator material for use in the formulation of the present invention is silica. A commercially available silica material is Min-U-Sil (trademark of Pennsylvania Glass Company, Pa.). Preferably, silica may be present in the formulation such that the acceleration of the clotting mechanism is substantially achieved while minimizing visual hemolysis or impacting chemistry analytes of the blood sample in an amount from about 40 to about 90 weight percent and most preferably at about 70 weight percent to about 95 weight percent.

An organic acid is also preferably used in the formulation of the present invention to initiate an effervescent reaction in the presence of water.

Desirably, the organic acid includes, but is not limited to, organic compounds containing at least one carboxylic acid functionality such as tartaric acid, citric acid, malic acid, maleic acid, fumaric acid, succinic acid, ascorbic acid and mixtures thereof.

The preferred organic acid for use in the formulation of the present invention is citric acid. Preferably, citric acid may be present in the formulation in an amount from about 5 to about 30 weight percent and more preferably at about 3 weight percent to about 15 weight percent.

A metal carbonate compound is also preferably used in the formulation of the present invention to initiate the disintegrating reaction in the presence of acid and water.

Preferably, the metal carbonate compound is water soluble and includes, but is not limited to an alkali metal salt, sodium bicarbonate, sodium carbonate, sodium sesquicarbonate, potassium carbonate, cadmium carbonate, calcium carbonate, rubidium carbonate, potassium bicarbonate, sodium benzoate, sodium phosphate monobasic and sodium glycine carbonate.

Most preferably the metal carbonate compound is an alkali metal salt. The preferred alkali metal salt for use in the formulation of the present invention is sodium bicarbonate. Preferably, sodium bicarbonate may be present in the formulation in an amount from about 5 to about 30 weight percent and more preferably at about 3 weight percent to about 15 weight percent.

The additive formulation may further comprise a binding agent from about 1 weight percent to about 30 weight percent.

Desirably, the pH of the formulation is from about 5 to about 9, preferably from about 6 to about 8 and most preferably from about 6.5 to about 7.5.

Most preferably the additive formulation of the present invention comprises:
   (a) about 70 weight percent to about 95 weight percent of a clot activator;
   (b) about 3 weight percent to about 15 weight percent of organic acid;
   (c) about 3 weight percent to about 15 weight percent of metal carbonate; and
   (d) about 4 weight percent to about 6 weight percent of a surfactant which is capable of inhibiting the adsorption of blood components to a blood collection device.

An alternate embodiment of the present invention includes a binding agent, the additive formulation comprising:
   (a) from about 40 weight percent to about 90 weight percent of a clot activator;
   (b) from about 5 weight percent to about 30 weight percent of an organic acid;
   (c) from about 5 weight percent to about 30 weight percent of a metal carbonate;
   (d) from about 2 weight percent to about 10 weight percent of a surfactant which is capable of inhibiting the adsorption of blood components to a blood collection device; and
   (e) from about 1 weight percent to about 30 weight percent of a binding agent.

Most preferably the alternate embodiment of the present invention comprises:
   (a) from about 70 weight percent to about 95 weight percent of a clot activator;
   (b) from about 3 weight percent to about 15 weight percent of an organic acid;
   (c) from about 3 weight percent to about 15 weight percent of a metal carbonate;

(d) from about 4 weight percent to about 6 weight percent of a surfactant which is capable of inhibiting the adsorption of blood components to a blood collection device; and (e) from about 1 weight percent to about 10 weight percent of a binder.

A binding or bulking agent may be used in the formulation of the present invention to provide binding and lubricating properties to the formulation.

Preferably, the binding agent includes, but is not limited to polyvinyl-pyrrolidone (PVP), polyvinyl-alcohol (PVA), polyethylene glycol (PEG), carboxymethyl cellulose or corn starch.

The preferred binding agent for use in the formulation of the present invention is polyvinylpyrrolidone (PVP). Preferably, PVP may be present in the formulation in an amount from about 1 to about 30 weight percent. Most preferably, PVP may be present in an amount from about 1 to about 10 weight percent.

A binding agent enables granulating of the formulation without the forming of a pellet.

Polyvinylpyrrolidone is soluble in water and in a number of polar and non-polar organic solvents. Polyvinylpyrrolidone therefore serves as a binder and as a lubricant. Therefore, when the pellet of the present invention is dissolved in water, there is substantially no insoluble residue.

The polyvinylpyrrolidone used in the present invention is a polymer of vinylpyrrolidone having a molecular weight of about 15,000 to about 200,000. PVP is soluble in water and is also soluble in many organic solvents such as aliphatic alcohols, chlorinated hydrocarbons, esters, nitroparaffins and amines.

Most preferably, the components of the formulation are in a physically bound form to maximize the dispersion of the formulation. They may be bound into pellets, pills, capsules, granules, tablets and the like may all be used in the practice of this invention. Most preferably, the formulation of the present invention is in pellet form. Pellet form is convenient because the formulation will rapidly disperse in the blood sample.

A dry compression technique may be used to form a pellet of the formulation of the present invention.

The dry compression technique consists of mixing the components of the formulation and then applying sufficient force to form a pellet. The heat of compression binds the dry powder together, to form a pellet. The pellet formulation of the present invention is prepared by mixing the ingredients in a standard shaker for about two (2) hours or until a fine blend mixture is obtained. Then small portions of the mixed batch of powder are aliquoted into a manual puncher. The manual puncher consists of a piston-cylinder assembly. Aliquoted powder is placed in the die cavity and force is applied by means of a hydraulic or pneumatic press. Typically, the aliquoting and pressing operations are automatically performed in commercially available tablet presses.

The surfactant is readily included in the additive preparation by a variety of means. Most desirably, the surfactant is dissolved in alcohol and coated onto the granulated clot activator powder. The surfactant could also be dispersed in water and coated onto the silica particles and then dry blended with the other components of the additive preparation. Alternately, the clot activator tablet, once formed by dry compression, could be coated with a solution or dispersion of the surfactant in alcohol. The alcohol, or alternate organic solvent or carrier, could be isopropanol, ethanol, methanol, etc. It is also within the scope of the invention to dry blend the surfactant, if it is a solid, with the other substances in the additive preparation.

Other ingredients which are conventional or desirable in various pellet formulations may also be added to the formulation as long as they do not adversely affect the overall properties of the formulation.

The additive preparation of the present invention is preferably located in a collection device. The device is most preferably a blood collection device with an inner surface substantially free of a surfactant-containing coating and may be either an evacuated blood collection device or a non-evacuated blood collection device. The collection device is desirably made of plastic, such as but not limited to polyethylene terephthalate, or polypropylene or glass.

The additive preparation of this invention provides good clotting performance and provides a collection device with a wall surface which is not fouled by excessive blood proteins and cells which can potentially interfere with clinical test results of serum analytes.

Furthermore, the additive preparation of the present invention can be prepared and subsequently tabletted offline and rapidly dispersed into a tube online, lowering the overall cycle time for production of a blood collection device which would otherwise require the time-consuming and labor-intensive steps of coating and drying the clot activator and surfactant onto the tube wall.

Referring to the drawings in which like reference characters refer to like parts throughout the several views thereof, FIG. 1 shows a typical blood collection device 10, having an open end 16, a closed end 18, inner wall 12, and a stopper 14 that includes a lower annular portion or skirt 15 which extends into and presses against the inner wall 12 of the tube for maintaining stopper 14 in place.

Figure 2:
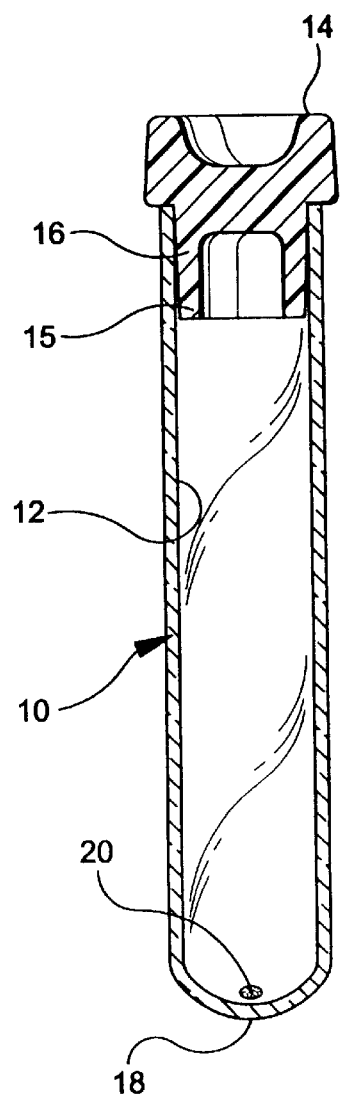
FIG. 2 is a longitudinal sectional view of the tube of FIG. 1 taken along line 2—2, comprising the additive formulation of the present invention.

FIG. 2 shows device 10 with an additive preparation 20.

A blood specimen sample of interest can be transferred into device 10, wherein the specimen contacts the additive so that the additive rapidly disperses into the specimen and clot activation is initiated.

The following examples are not limited to any specific embodiment of the invention, but are only exemplary.

Examples 1–6 and Tables 1–7 relate to the additive preparation disclosed in U.S. application Ser. No. 08/911, 394 to Cohen and Dastane which does not contain a surfactant agent, but which otherwise contains the same components as the present invention. In particular, Examples 1–4 and Tables 1–5 demonstrate the complete dispersion in a fluid of a silica clot activator and the excellent clotting performance which results from an effervescent dispersion of the silica. The results further demonstrate that the use of a disintegrant material such as sodium bicarbonate does not have an adverse impact on analyte values. Examples 5 and 6 and Tables 6 and 7 demonstrate the excellent anticoagulent performance which results from the effervescent dispersion of the anticoagulent ethylenediaminetetraacetic acid. Example 7 and Tables 8 and 9, which relate to the additive preparation of the present invention, demonstrate that the surfactant agent included in the additive formulation of the present invention is at least as effective at preventing visible adhesion of blood components as control tubes which contain inner walls pre-coated with surfactant.

EXAMPLE 1

Preparation of Additive Formulation

The additive formulation of the invention disclosed in U.S. application Ser. No. 08/911,394 was prepared with the following ingredients as listed in Table 1. This formulation does not contain the surfactant agent which is included in the formulation of the present invention.

TABLE 1

| Ingredients | Weight Percent (%) | Grams (gm) |
| --- | --- | --- |
| silica (Min-U-Sil, Pennsylvania Glass Company) | 50 | 1.05 |
| baking soda (Mixture of sodium bicarbonate and tartaric acid, Mfg: Arm and Hammer) | 48 | 1.0 |
| citric acid (Sigma Chemicals Catalog No. C1909, Lot No. 45H0868) | 2 | 0.05 |

In a mixing vessel, all of the above ingredients were mixed together. The mixture was then blended using a mortar and pestle for about 20 minutes or until a fine blend was obtained. Twenty (20) pellets weighing approximately 1.25 mg each were formed using a puncher. Because of the manual force applied on the puncher during the aliquoting process the powdered material formed into a pellet.

EXAMPLE 2

Effectiveness Evaluation of Additive Formulation

This example demonstrates the effective distribution of the silica clot activator in blood which results from the effervescence of the formulation shown in Table 1.

The effectiveness of the preparations of Example 1 were assessed by measuring the amount of silica available in the supernatant of added water. In other words, the measurement of silica not sedimented at the bottom of the tube whereby the silica in the supernatant represents silica available for clotting in the blood.

The pellets prepared in Example 1 were added to twenty 16×100 mm plastic tubes. These twenty tubes were separated into groups of ten, Group A and Group B. Group C consisted of the control tubes, twenty 13×100 mm plastic tubes with a wall coating consisting of a mixture of silica, PVP and surfactant and a gel at the bottom. These tubes are VACUTAINER® brand PLUS tubes.

The 16×100 mm tubes used in this experiment were marked for 8 ml fill. There was also a second mark on these tubes, placed near the closed or bottom end of the tube. The bottom mark acted as an indicator for pipetting water from the tube, without disturbing the sedimented silica. This ensured that silica that is at the bottom of the tube is not aspirated along with the supernatant, thus giving falsely elevated numbers for amount of silica in the solution.

These twenty tubes were further separated into groups of ten tubes each. The reason for the two separate groups was during the experiment one group was to be mixed while other one remained unmixed.

For controls, twenty 13×100 mm plastic tubes with wall coating consisting of a mixture of silica, PVP, and surfactant were used (VACUTAINER® brand PLUS tubes, Lot # DG061096tI). These tubes also had gel at the bottom of the tube. These tubes were also separated into groups of 10 each.

De-ionized (DI) water was added to all the prototype and control tubes, one tube at a time. For the unmixed set of tubes, the DI water was immediately pipetted out. Nephelometry (Hach Turbiditimeter), which measures the amount of suspended particles, was done on these collected samples immediately. For the mixed tubes the methodology used was identical, except mixing with five inversions was done before pipetting the DI water.

Table 2 lists the amount of silica per mL of water in the supernatant. The data clearly indicates that the pellets in both mixed and unmixed conditions outperformed the wall coated tubes.

TABLE 2

SILICA IN SUPERNATANT (SAMPLE SIZE, N = 10)

| Tube Type | Handling Condition (#of Inversions) | Amt. of Silica dispensed (mg/mL) | Amt. of silica in the Supernatant (mg/mL) | (wt %) |
| --- | --- | --- | --- | --- |
| Prototype | 0 | 0.08 | 0.07 | 87.5 |
| Control | 0 | 0.15 | 0.05 | 33.33 |
| Prototype | 5 | 0.08 | 0.1* | 100 |
| Control | 5 | 0.15 | 0.09 | 60 |

EXAMPLE 3

Preparation of Additive Formulation

The additive formulation of the invention disclosed in U.S. application Ser. No. 08/911,394 was prepared with the following ingredients as listed in Table 3. This formulation does not contain the surfactant agent which is included in the formulation of the sent invention.

TABLE 3

| Ingredients | Weight Percent |
| --- | --- |
| Silica | 50 |
| sodium bicarbonate | 25 |
| citric acid | 25 |

EXAMPLE 4

Clinical Efficacy of the Pellets

This example demonstrates that pellets made using the formulation in Example 3 provide complete clotting of blood samples. The example further demonstrates that the use of the sodium bicarbonate disintegrant material does not adversely impact analyte values.

To demonstrate the clinical efficacy of the dispersion of the pellets in Example 3, a five donor clinical study of human donors was performed and the clotting performance and select analytes of the samples were evaluated.

The measure of clotting performance was visual evaluation for gelation of blood as well as presence of fibrin mass post centrifugation. The presence of fibrin mass after centrifugation demonstrates an incomplete clotting process even if the blood has completely gelled prior to centrifugation. In this experiment the prototype and control tubes were centrifuged for 10 minutes after waiting for 15 minutes post specimen collection.

Table 4 lists the visual observations done for clotting, while Table 5 lists the results from the analyte measurements done on these tubes.

TABLE 4

VISUAL OBSERVATIONS (SAMPLE SIZE, N = 5)

| Tube Type | Number of Tubes not Clotted before Centrifugation | Fibrin Mass |
|---|---|---|
| Prototype (Formulation per Example 3)(13 × 100 mm plastic tube with first coat of surfactant, Pellet wt. = 1.5 mg) | 1 | 2 |
| Control-1 (Glass, 13 × 100 mm tube with wall coated silica) | 5 | 5 |
| PLUS Control (Plastic, 13 × 100 mm tube with wall coated silica) | 2 | 5 |

TABLE 5

(Part of Example 4)
MEAN OF MEASURED ANALYTES
(SAMPLE SIZE, N = 5 FOR EACH TUBE TYPE)

| Analyte | Glass Control | Plastic Control | Prototype |
|---|---|---|---|
| Sodium (mmol/L) | 139 | 138.8 | 139.6 |
| Potassium (mmol/L) | 4.02 | 4.02 | 4.06 |
| Chloride (mmol/L) | 100.4 | 100.6 | 100 |
| $CO_2$ (mmol/L) | 27.2 | 27.6 | 27.8 |
| LD (IU/L) | 421.6 | 427.6 | 425.4 |
| PH | 7.62 | 7.61 | 7.59 |

In Table 4, it is important to note that in all cases when fibrin was present in the prototype tubes, the size of the fibrin masses was markedly smaller than those presented by the corresponding control tubes. This was an indication of more complete clotting in the prototype tubes. In Table 5, the results from the analytes demonstrated medically significant differences compared with the control products. This demonstrates that the use of disintegrant material does not have an adverse impact on analyte values.

EXAMPLE 5

Preparation of Additive Formulation

The additive formulation of the invention disclosed in U.S. application Ser. No. 08/911,394 was prepared with the following ingredients as listed in Table 6. This formulation does not contain the surfactant agent which is included in the formulation of the present invention.

TABLE 6

| Ingredients | Weight Percent |
|---|---|
| Ethylenediaminetetraacetic acid dipotassium salt ($K_2$EDTA) (Anticoagulant) (Mfg.: SIGMA Chemicals, Lot #14H0457) | 50 |
| Citric Acid Monohydrate (Mfg.: SIGMA Chemicals, Lot #115H1018) | 16.33 |
| Sodium bicarbonate (Mfg.: SIGMA Chemicals, Lot #56H0423) | 33.67 |

In a mixing vessel, all of the above ingredients were mixed together. The mixture was then blended using a mortar and pestle for about 30 minutes or until a fine blend was obtained. Pellets weighing between about 7 to 8 mg each were formed using a puncher. Because of the manual force applied on the puncher during the aliquoting process the powdered material formed into a pellet.

EXAMPLE 6

Clinical Efficacy of the Additive Formulation

This example demonstrates that pellets made using the formulation in Example 5 provide excellent anticoagulent performance.

To demonstrate the clinical efficacy of the additive, the pellets made according to Example 5 were evaluated for anticoagulant performance. Three 13×75 mm plastic evacuated tubes of 2 ml draw each containing one pellet as made in Example 5 were used to collect blood from 3 human donors. The tubes were then evaluated for anticoagulant performance. The method for evaluating anticoagulant performance was by visual inspection for gelation of blood, as well as by observing microclots when the blood specimen is filtered through a fine meshed sieve. Any observation of visual clotting and/or the presence of microclots was deemed a failure. Table 7 shows the results from the clinical study.

TABLE 7

| Tube Type | Handling Condition | Number of Tubes that Passed |
|---|---|---|
| Prototype (formulation per Example-5 in 13 × 75 mm plastic evacuated tube, 2 mL draw) | no mixing | 3 |
| Control #1- (VACUTAINER brand tubes, cat # 367648, 2 mL draw, $K_2$EDTA sprayed on the tube wall) | no mixing | 1 |
| Control #2 - (VACUTAINER brand tubes, cat #367648, 2 mL draw, $K_2$EDTA sprayed on the tube wall) | mixed by inverting tube 10 times | 3 |

EXAMPLE 7

This example shows that the inclusion of a surfactant agent in the preparation of the present invention effectively reduces the amount of adhesion of blood components as compared to the same preparation without the surfactant. Furthermore, this example demonstrates that the surfactant-containing preparation of the present invention is at least as effective at preventing visible adhesion of blood components as control tubes which contain inner walls precoated with surfactant.

The additive preparations of the present invention were prepared with the following components as listed in the tables below:

TABLE 8

Prototype Preparation #1

| Ingredient | Weight Percent (%) |
|---|---|
| Silica (Min-U-Sil, Pennsylvania Glass Company) | 81 |
| Sodium bicarbonate | 9 |

TABLE 8-continued

Prototype Preparation #1

| Ingredient | Weight Percent (%) |
| --- | --- |
| Citric Acid | 7 |
| PVP | 1 |
| Silicone surfactant (Silwet ® L-720, CK Witco Corporation) | 2 |

TABLE 9

Prototype Preparation #2

| Ingredient | Weight Percent (%) |
| --- | --- |
| Silica (Min-U-Sil, Pennsylvania Glass Company) | 73 |
| Sodium bicarbonate | 9 |
| Citric Acid | 7 |
| PVP | 1 |
| Silicone surfactant (Silwet ® L-720, CK Witco Corporation) | 10 |

Tablets were formed from these preparations as well as from analogous preparations not containing the silicone surfactant. These prototype tablets were dispensed into surfactant-free VACUTAINER® brand PLUS tubes of size 16×10 mm. Three tubes containing each preparation were made. The tubes were subsequently sterilized by cobalt irradiation prior to blood collection.

The prototype tubes and conventional VACUTAINER® brand PLUS tubes containing surfactant-coated walls (controls) were used for human blood collection. After collection, the control tubes were, by convention, inverted 5 or more times, and the blood was allowed to clot for at least 30 minutes. The prototype tubes were not inverted, but otherwise handled similarly. The tubes were then spun in a centrifuge at about 1000 G for 10 minutes. The tubes were subsequently removed from the centrifuge and inspected.

The control tubes had a light layer of "red-cell" film but did not show any significantly visible adhesion of blood components, such as red cells, in the serum phase of the blood (red-cell hang-up). The prototype tubes containing the additive preparation without the silicone surfactant showed large amounts of film and hang-up. However, when the additive preparation included the silicone surfactant of the present invention, there was very light film in trace amounts, and red-cell hang-up was minimal with just a spot or a trace. The results were equivalent for prototypes #1 and #2. The example illustrates that the surfactant need not be coated on the tube wall to be effective in preventing adhesion of blood components.

What is claimed is:

1. An assembly for collecting a body fluid, comprising a container, and
a additive preparation in the container, the additive preparation comprising an organic acid, a metal carbonate compound, a surfactant, and an additive selected from the group consisting of a clot activator, an anticoagulant, and a urine preservation compound.

2. The assembly of claim 1 wherein the surfactant reduces the surface tension of a body fluid to about 50 dynes/cm.

3. The assembly of claim 2 wherein the body fluid is blood.

4. The assembly of claim 1 wherein the surfactant reduces the surface tension of a body fluid from about 30 dynes/cm to about 45 dynes/cm.

5. The assembly of claim 1 wherein the surfactant is a silicone.

6. The assembly of claim 5 wherein the silicone surfactant comprises a hydrophobic backbone of polydimethylsiloxane and a hydrophilic tail of polyalkylether.

7. The assembly of claim 5 wherein the silicone surfactant is present at about 2 weight percent to about 10 weight percent of the preparation.

8. The assembly of claim 1 further comprising a binding agent in the additive preparation.

9. The assembly of claim 8 wherein the binding agent is selected from the group consisting of polyvinylpyrrolidone, polyvinyl-alcohol, polyethylene glycol, carboxymethyl cellulose and corn starch.

10. The assembly of claim 1 wherein the organic acid is selected from the group consisting of citric acid, tartaric acid, malic acid, maleic acid, fumaric acid, succinic acid, ascorbic acid, and mixtures thereof.

11. The assembly of claim 1 wherein the metal carbonate compound is an alkali metal salt.

12. The assembly of claim 11 wherein the alkali metal salt is selected from the group consisting of sodium bicarbonate, sodium carbonate, sodium sesquicarbonate, potassium carbonate, cadmium carbonate, calcium carbonate, potassium bicarbonate, sodium benzoate, sodium phosphate monobasic and sodium glycine carbonate.

13. The assembly of claim 10 wherein the alkali metal salt is sodium bicarbonate.

14. The assembly of claim 1, wherein the preparation contains about 40 to about 90 weight percent of the additive.

15. The assembly of claim 1, wherein the container is an evacuated tube.

16. An assembly for collecting a body fluid, comprising a container, and
an additive preparation in the container, the additive preparation comprising:
(a) from about 40 weight percent to about 90 weight percent of an additive selected from the group consisting of a clot activator, an anticoagulant, and a urine preservation material;
(b) from about 5 weight percent to about 30 weight percent of an organic acid;
(c) from about 5 weight percent to about 30 weight percent of a metal carbonate compound; and
(d) from about 2 weight percent to about 10 weight percent of a surfactant.

17. The assembly of claim 16 wherein the surfactant is a silicone.

18. The assembly of claim 17 wherein the silicone surfactant comprises a hydrophobic backbone of polydimethylsiloxane and a hydrophilic tail of polyalkylether.

19. The assembly of claim 16, wherein the preparation further comprises about 1 weight percent to about 30 weight percent of a binding agent.

20. The assembly of claim 16 wherein the organic acid is selected from the group consisting of citric acid, tartaric acid, malic acid, maleic acid, fumaric acid, succinic acid, ascorbic acid and mixtures thereof.

21. The assembly of claim 16 wherein the metal carbonate compound is an alkali metal salt.

22. The assembly of claim 16, wherein the container is an evacuated tube.

* * * * *